(12) United States Patent
Marshall et al.

(10) Patent No.: US 6,887,429 B1
(45) Date of Patent: May 3, 2005

(54) APPARATUS AND METHOD FOR AUTOMATED MEDICAL DIAGNOSTIC TESTS

(75) Inventors: Graham D. Marshall, Fox Island, WA (US); Duane K. Wolcott, Fox Island, WA (US); Daniel Ericson, Rochester, MN (US); Don C. Olson, Gig Harbor, WA (US)

(73) Assignee: Global FIA, Gig Harbor, WA (US)

( * ) Notice: Subject to any disclaimer, the term of this patent is extended or adjusted under 35 U.S.C. 154(b) by 445 days.

(21) Appl. No.: 09/771,314

(22) Filed: Jan. 26, 2001

(51) Int. Cl.[7] .................. G01N 21/00; G01N 31/00; B01L 3/02; B01L 11/00
(52) U.S. Cl. ............... 422/81; 422/67; 422/62; 422/58; 422/50; 422/103; 422/68.1; 422/100; 436/180; 436/174; 436/43; 73/863.01; 73/863.41; 73/864.74; 73/864.81
(58) Field of Search ................ 422/100, 81, 82, 422/68.1, 67, 63, 110, 62, 89, 58, 50, 103; 436/180, 174, 43, 53; 73/863.01, 863.11, 863.41, 863.44, 864.74, 864.81, 864.9

(56) References Cited

U.S. PATENT DOCUMENTS

| | | | |
|---|---|---|---|
| 4,244,919 A * | 1/1981 | Chen ............... | 422/100 |
| 4,774,057 A * | 9/1988 | Uffenheimer et al. ....... | 422/100 |
| 4,952,372 A | 8/1990 | Huber | |
| 5,104,808 A * | 4/1992 | Laska et al. .......... | 436/48 |
| 5,171,538 A * | 12/1992 | Tremmel et al. ......... | 422/100 |
| 5,248,616 A * | 9/1993 | Beckman et al. ........ | 436/116 |
| 5,399,497 A * | 3/1995 | Kumar et al. .......... | 436/53 |
| 5,425,921 A * | 6/1995 | Coakley et al. ......... | 422/102 |
| 5,447,691 A * | 9/1995 | Sanuki ............... | 422/100 |
| 5,558,838 A * | 9/1996 | Uffenheimer .......... | 422/100 |
| 5,561,069 A * | 10/1996 | Brigham-Burke et al. .. | 436/518 |
| 5,695,720 A | 12/1997 | Wade et al. | |
| 5,837,203 A * | 11/1998 | Godec et al. .......... | 422/100 |
| 5,849,592 A | 12/1998 | Pollema et al. | |
| 6,033,628 A * | 3/2000 | Kaltenbach et al. ...... | 422/68.1 |
| 6,040,186 A * | 3/2000 | Lewis et al. .......... | 436/53 |
| 6,054,326 A * | 4/2000 | Dubus ............... | 436/180 |
| 6,149,872 A * | 11/2000 | Mack et al. .......... | 422/102 |
| 6,190,614 B1 * | 2/2001 | Fukunaga ............ | 422/100 |
| 6,315,952 B1 * | 11/2001 | Sklar et al. .......... | 422/63 |
| 6,344,172 B1 * | 2/2002 | Afeyan et al. ......... | 422/70 |
| 6,365,107 B1 * | 4/2002 | Markelov et al. ....... | 422/83 |
| 6,416,718 B1 * | 7/2002 | Maiefski et al. ........ | 422/103 |
| 6,488,897 B2 * | 12/2002 | Dubrow et al. ........ | 422/102 |
| 6,495,104 B1 * | 12/2002 | Unno et al. .......... | 422/68.1 |
| 2001/0053337 A1 * | 12/2001 | Doktycz et al. ........ | 422/100 |
| 2003/0156989 A1 * | 8/2003 | Safir et al. ........... | 422/99 |
| 2004/0043499 A1 * | 3/2004 | Lee-Alvarez .......... | 436/146 |

* cited by examiner

Primary Examiner—Jill Warden
Assistant Examiner—Brian R. Gordon
(74) Attorney, Agent, or Firm—Perkins Coie LLP

(57) ABSTRACT

A method and apparatus for the automation of existing medical diagnostic tests is described. This method, called sequential injection analysis, makes use of a pump, multi-position selection valve, and micro-bore tubing to automate sample manipulation and reagent addition. A suitable detector with a flow cell also forms part of the flow manifold and this detector is used to measure some parameter that can be related to the desired diagnostic measurement. A reagent cartridge suitable for storing and reconstituting lyophilized reagent or reagent concentrate is also described. Use of such a reagent cartridge further enhances the automation of the device by providing a means for preparing reagents in an automated fashion. Automation of the measurement sequence and the sequencing of tests are controlled by a suitable central processor unit and software. The apparatus provides a means of automating existing manual diagnostic tests and as yet, undefined tests.

2 Claims, 6 Drawing Sheets

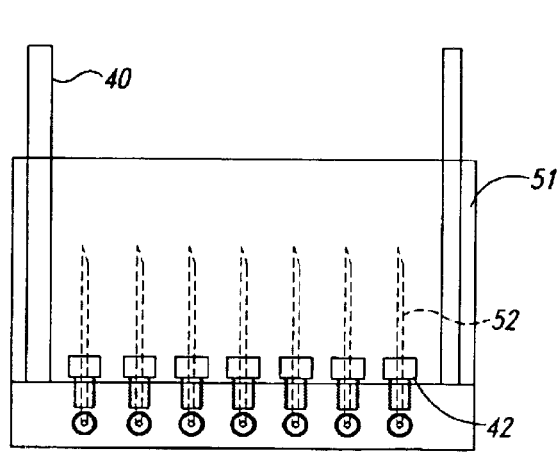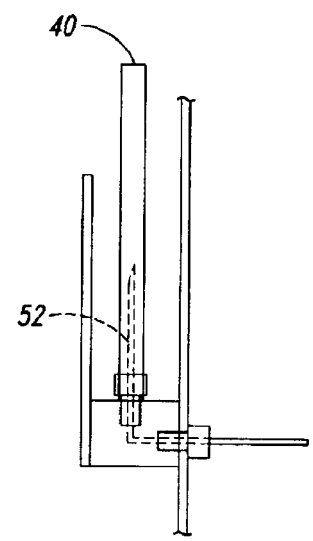
Fig. 4
Fig. 5
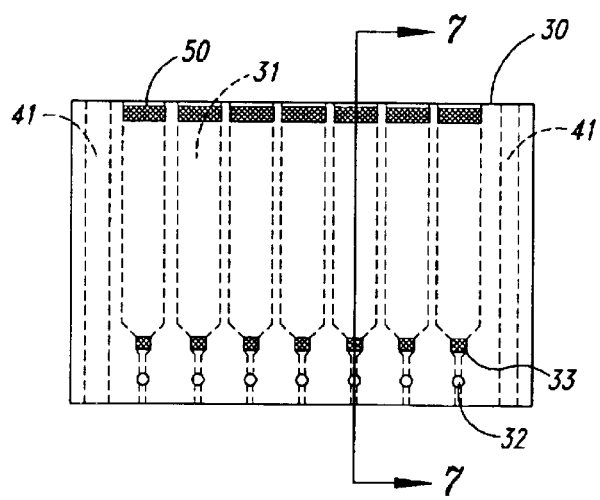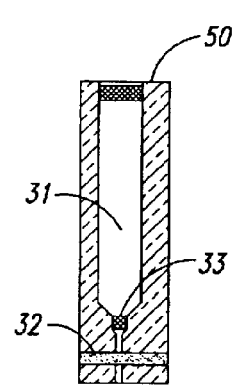
Fig. 6
Fig. 7

APPARATUS AND METHOD FOR AUTOMATED MEDICAL DIAGNOSTIC TESTS

TECHNICAL FIELD

This invention relates to techniques, methods, and apparatus for the automation of medical diagnostic tests. More particularly, the invention relates to apparatus and methods for the use of Sequential Injection Analysis (SIA) for the automation of medical diagnostic tests. Several examples are given illustrating the application of this invention to the automation of selected medical diagnostic test.

BACKGROUND OF THE INVENTION

As early as 1966, Skeggs described air-segmented continuous flow analysis. This approach to serial assays involved the introduction of successive samples into a length of tubing. Reagents are added at strategic points and mixing and incubation take place while the sample is on its way to the flow cell of the detector. Intermixing of adjacent samples is prevented by the introduction of air bubbles into the flow between samples. The first system was developed for the determination of glucose and urea in blood.

Flow injection analysis (FIA) represented a significant advancement in the automation of wet chemical analysis procedures. FIA has been described as a simple and versatile analytical technology for automating wet chemical analysis, based on the physical and chemical manipulation of a dispersed sample zone formed from the injection of the sample into a flowing carrier stream and detection downstream. FIA avoids the use of bubbles to separate samples. Examples of FIA systems and apparatus are described in U.S. Pat. Nos. 4,952,372 and 5,695,720, which are incorporated herein in their entirety by reference thereto.

The power of FIA as an analytical tool lies in its ability to combine sampling, sample processing, and detection in a wide variety of different ways to create a broad range of different methodologies, and perform these methodologies rapidly and automatically with minute amounts of sample. The device most commonly used to measure out the sample and insert it into the FIA carrier stream is a two-position sample injection valve. Peristaltic pumps are frequently used to propel streams in the flow injection manifold. Many detection techniques have been applied to FIA.

Sequential Injection Analysis (SIA) was developed in response to the requirement for a more rugged and simple apparatus suitable for automation within industrial applications. Like FIA, SIA is an automated approach to sample handling that allows the convenient automation of different manual wet-chemistry procedures to provide rapid, precise, and accurate measurements. Small solution zones are manipulated under controlled dispersion conditions in narrow bore conduits, typically tubing. SIA systems and apparatus are discussed in U.S. Pat. No. 5,849,592, which is incorporated herein in its entirety by reference thereto.

While, like FIA, SIA is fundamentally dependent on the dispersion of zones in a flowing stream, conceptually, the practice of SIA is different from FIA. Where FIA is dependent on the physical dimensions of a sample loop, SIA makes use of an accurate metering pump to assemble a stack of precisely measured sample and reagent zones selected using a multi-position selection valve and a holding coil. Flow reversal and passage through the micro-bore tubing of the SIA manifold ensures intimate mixing of sample and reagent zones to form a detectable species. Different mixing strategies can be achieved using the same SIA system. Accordingly, SIA systems can easily and quickly switch between different tests of sample and reagent zones for a selected species. In FIA, swapping to a different test frequently requires a time and labor intensive change to the manifold hardware. In SIA on the other hand, this can be accomplished simply by a change in the flow-control sequence and in some cases the detector.

SIA has several advantages over FIA. Reagent use is drastically reduced. Typical FIA experiments make use of at least 1 ml of reagent per measurement. SIA typically makes use of less than 100 $\mu$l. Tubing manifolds are simple and robust typically comprising a pump, selection valve, and connected by a flow conduit such as micro-bore tubing. The same manifold can be used for widely different chemistries simply by changing the flow sequence rather than the plumbing. Analyzer maintenance is therefore simplified and the same manifold can be used for tests that require quite different sample handling strategies. The selection valve replaces the injection valve and provides a means for selecting different sample streams and calibrants. This enables a convenient means of swapping from one test to the next and automating the calibration of the apparatus.

A basic SIA system comprises a high precision pump to meter and propel sample and reagent zones within the system, a multi-position selection valve, micro bore tubing in the form of at least a holding coil and possibly a reaction coil or other suitable flow conduit, and a detector or detectors equipped with suitable flow through cells. Most often, a LED-based photometer is used as the detector, but the practice of SIA is not limited to these simple devices and transducers that make both physical and chemical measurements have been used. The selection valve has multiple ports that can be used for connection to selected reagents reservoirs, sample streams, calibration standards, and one or more detectors. While the flat plate rotary design of multi-position selection valves has been widely used, other stream selection manifolds could serve equally well. Because of their excellent accuracy and pulseless flow, syringe pumps are most frequently used in SIA.

Although the reagent can be included in the carrier stream, more often than not, the reagent is loaded as a separate zone. Then the syringe is filled with a simple carrier solution or chemical buffer solution. This carrier solution has several functions. It is used to propel reactants and reaction products in the flow manifold. The carrier solution is also used to create a chemical environment conducive to the measurement chemistry, e.g. by adjusting the pH or ionic strength of the reaction media. It also is useful in flushing the flow manifold so that there is no carry over or cross-contamination from one sample to the next. Because the detector is exposed to this clean solution for the majority of the time, fouling is minimized.

After the sample zone has been drawn up into the holding coil, the selection valve is advanced to a port connected to a reagent reservoir and a small reagent zone is drawn up into the holding coil. In this way it is possible to construct a stack of well defined zones which, when the sample and reagent are mixed together, give rise to a detectable species. Accurate measurement of sample and reagent zones necessitates repeatable and accurate control of the timing of component events. Once developed a suitable controller slavishly repeats the measurement sequence to give reproducible results. Different results can be achieved by changing the sequence of reagent and sample selection.

The successful implementation of SIA hinges on the reproducible mixing of a well-defined stack of reagent and sample zones. The mixing of these initially distinct zones is achieved through controlled dispersion in the reaction coil and reversal of the flow in the holding coil. Optimum sensitivity is achieved when mixing is maximized and axial dispersion is minimized. For this reason, reactors incorporated in the apparatus frequently make use of a geometric arrangement that ensures rapid and frequent changes in direction.

The existing art in the field of medical diagnostic tests is extensive. In this regard, enzyme-linked immunosorbent assays (ELISA) enjoy ubiquitous application. Countless methods and chemistries have been developed for a wide range of medical diagnostic tests and are available in kit form. Many of these rely on manual introduction of reagent components using hand held micropipettes. Robotic methods have been applied to the automation of these tests, and segmented-flow analysis techniques have been applied to medical diagnostic tests. While these methods and chemistries are highly beneficial for selected tests and techniques, advances in the automation and methods of medical diagnostic tests are still in need.

SUMMARY OF THE INVENTION

The present invention provides improvements, for example, to apparatus for and methods of medical diagnostic tests, utilizing SIA techniques. One embodiment of the present invention provides an improved system for use in medical diagnostic tests, and the system includes a central processing unit (CPU) control, software-based sequence controller, an SIA apparatus, and disposable or reusable reagent cartridges releasably connected to the SIA apparatus. One embodiment of the invention includes a disposable reagent pack that can be used in an automated fashion to reconstitute lyophilized reagents or dilute reagent concentrates. Embodiments of the invention utilize micro-bore tubing in the system; although other embodiments include conduits of various materials and dimensions.

In one embodiment, multiple detectors and a range of reagents can be accessed in the SIA apparatus, thereby simultaneously performing more than one test. For tests requiring longer incubation times, the system with the SIA apparatus and the reagent cartridge provides a means of optimizing the use of the hardware to perform several different tests simultaneously. Some tests, for example the determination of blood clotting time, include sequence steps that have a varying duration. The sequencing of events under such conditions are monitored, controlled and accomplished by the CPU and a selected sequencing process of the sequence controller that selectively control selection of reagents and the sample flow in the SIA apparatus. The same system is used to perform a test and provide a single measurement.

Furthermore, by employing one or more disposable reagent cartridges containing lyophilized reagents or reagent concentrate that are automatically reconstituted or diluted using the apparatus components, the resultant system is suitable for use in a wide variety of application areas including the laboratory, operating room, and point-of-care environments. Use of such reagent cartridges reduces the minimum required technical expertise of users by automating the preparation of reagents. Furthermore, the reagent cartridge can be equipped with a machine readable barcode, symbology, or other identifying mechanism that can be used to provide data about the reagents in the cartridge to the analyzer for controlling or identifying which analysis to perform.

In another embodiment of the invention, the system includes a fully automated controller utilizing task-based software for controlling the SIA apparatus' tasks during entire testing sequences. These tasks include measurement of sample, preparations of reagents, priming of multi-position value (e.g., with the fresh reagent), controlling instrument warm up procedure, instrument calibration, instrument flush-out, and transition between different measurement suites. This system with the fully automated controller can be combined with the disposable or reusable reagent cartridge for ease and convenience of use. An embodiment of the invention includes computer algorithms for optimizing the sequencing of one or more tests carried out on a single apparatus.

BRIEF DESCRIPTION OF THE DRAWINGS

FIG. 4 is an enlarged front elevation view of a reagent cartridge mounting bracket of the reagent cartridge assembly in the SIA system of FIG. 1.

FIG. 5 is a side elevation view of the mounting bracket of FIG. 4.

FIG. 6 is an enlarged front elevation view of a disposal or reusable reagent cartridge of the reagent cartridge assembly of FIG. 3, the reagent cartridge being releasably mountable in the mounting bracket of FIG. 5.

FIG. 7 is a cross-sectional view taken substantially along lines 7—7 of FIG. 6 showing the reagent cartridge.

DETAILED DESCRIPTION

In the following description, certain specific details are set forth in order to provide a thorough understanding of various embodiments of the invention. However, one skilled in the art will understand that the invention may be practiced without these details. In other instances, well-known structures associated with Sequential Injection Analysis (SIA) apparatus and medical diagnostic tests have not been shown or described in detail to avoid unnecessarily obscuring the description of the embodiments of the invention.

Figure 1:
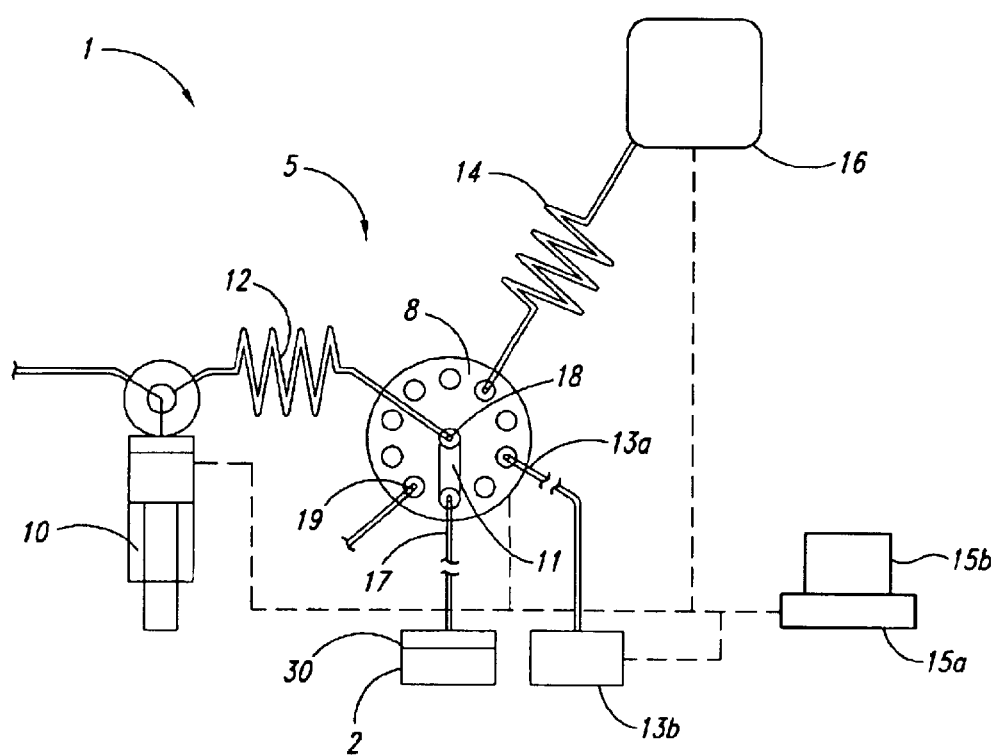
FIG. 1 illustrates an SIA test system in accordance with an embodiment of the present invention.

SIA offers significant advantages to the automation of these medical diagnostic tests. These advantages include reduction of manpower requirements, the possibility of moving the measurement closer to the patient, on-line real time monitoring of a patient during a medical procedure, the minimization of reagent usage and waste generation, and a reduction of exposure of medical personnel to bio-fluids such as blood. In the application of SIA to the automation of medical diagnostic tests in accordance with an embodiment of this invention, an SIA testing system 1 is assembled as schematically illustrated in FIG. 1. The SIA testing system 1 includes an SIA assembly 5 having at least one stream propulsion and metering device such as a syringe pump 10, a multi-position selection valve 8 coupled via fluid conduits to one or more reagents stream line 17, one or more sample stream line 13a, and one or more detectors 16. In one embodiment the syringe pump 10 is a Cavro Syringe pump, and the multi-position selection valve 8 is a valve manufactured by Valco Instrument Company of Houston, Tex. In alternate embodiments, other stream selection devices other than a multi-position selection valve could be used. The illustrated selection valve 8 has a single central port 18 and ten outer ports 19 arranged in a circle around the central port. A connecting channel 11 is in fluid communication with the central port 18 and can be rotated to select one of the surrounding outer ports 19. In this way, fluids can be accessed from one of the surrounding outer ports 19 via the central port 18 or pumped from the central port 18 to one of the surrounding outer ports 19. In FIG. 1, some of the ports (18 and 19) are shown with flow conduits coupled to them and some are shown empty.

The SIA assembly 5 includes a holding or reaction coil 12 in fluid connection between the syringe 10 and the multi-position valve 8 that has interior passageways forming a portion of the fluid path in the system. The SIA assembly 5 also has another reaction coil 14 in fluid communication between the multi-position valve 8, the detector 16, and a reaction cartridge assembly 2, discussed in greater detail below. The CPU 15a and the sequencing controller 15b are configured to control operation of the system in performing at least one medical diagnostic test, and in some embodiments multiple medical diagnostic tests simultaneously.

Figure 2:
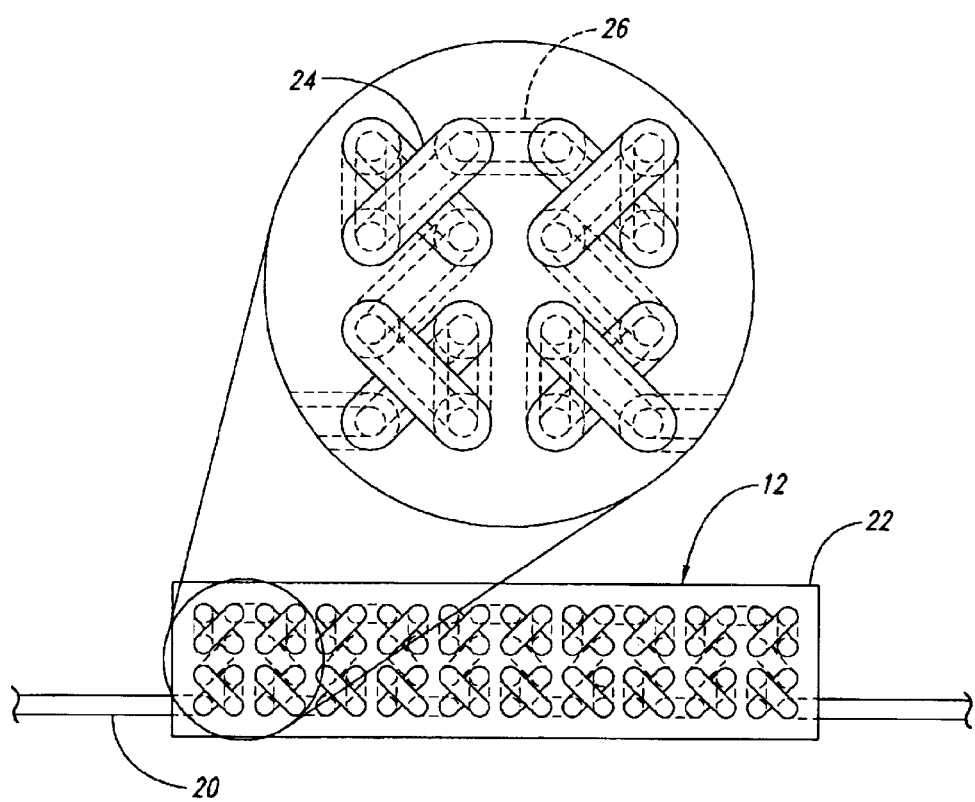
FIG. 2 is an enlarged top plan view of a reactor of the SIA system of FIG. 1 showing an internal flow pathway (in hidden lines) that ensures rapid and frequent changes in flow direction.

In some embodiments of the system, the temperature of the fluid conduits interconnecting the system's components may be controlled so that the sample and reagent zones experiences either an elevated temperature or a temperature below ambient as they pass therethrough. This is typically achieved by controlling the temperature of one or both of the reaction coils (12 and 14). While the term coil is used, various geometric arrangements of the flow conduits are included within the scope of this invention. The reaction coils (12 and 14) of the illustrated embodiment are represented by a reactor shown in FIG. 2 (available from Global FIA, Gig Harbor, Wash.) having a tortuous internal passageway constrained to a physical arrangement that ensures rapid and frequent changes in flow direction of fluids pumped through the reactor. The narrow bore tubing 20 is knotted onto a flat platen 22 to form this tortuous internal passageway.

In manual or ELISA medical diagnostic tests, sample and reagents are volumetrically dispensed into a suitable receptacle. After mixing, and some change in the resultant mixture that can be used to quantify a component of interest a suitable transducer is used to measure a response. The SIA testing system 1 of the present invention provides a means of automating this process.

In a simple test, for example, a small volume (typically between 5 and 100 µl) of sample from a sample source 13b is drawn through the sample stream line 13a into the holding coil 12 via a selected alignment of the multi-position valve 8 and the activation of the syringe pump 10. The volume of this sample zone is accurately metered by the syringe pump 10. The multi-position stream selection device 8 is then advanced to another outer port 19 linked by the reagent stream line 17 forming a narrow-bore to a reagent cartridge assembly 2. A volume of reagent is drawn from the reagent cartridge assembly 2 through the stream selection device 8 and into the holding coil 12. In some instances, it is desirable to draw the reagent first and then the sample. The direction of flow of the sample and reagent is then reversed and the stack of zones assembled in the holding coil 12 or reactor is propelled toward the detector 16. In the process, mixing between the sample and reagent zones is promoted. Further steps prior to detection where other reagents are added, reactants are heated or cooled, reactants are allowed to incubate for a controlled duration, reaction is promoted by illumination with ultra violet radiation or some other radiation fall within the scope of the invention. Flow rate and the pressure within the system are selectively set to a level that suits the measurement conditions for the selected diagnostic test.

The components of the SIA assembly 5 and the disposable reagent cartridge are controlled by the CPU 15a and the sequence controller 15b. In this way, reaction products are formed within the SIA test system 1 that can be detected by the detector 16. Finally, the reaction products are passed through the flow cell of the detector 16 and the detector response is recorded by the CPU 15a. The resultant signal is typically a peak or can be transformed into a peak. Peak height, area, width, or the time of the peak can be related to concentration or otherwise analyzed. Most often peak height is used. Peak width is useful when the flow cell is so designed as to allow a titration to take place.

In a typical series of tests, calibration standards with a known composition or physical characteristic are measured using the SIA test system 1. In this regard, one or more of the selection valve's outer ports 19 can be assigned to calibration standards that are treated in the same way as the sample. In such an embodiment, the CPU 15a or sequence controller 15b selects one of the standard ports in place of the sample port. Further, the same measurement sequence is followed. The resultant response is plotted against concentration or test parameter, and an appropriate calibration curve is established. Samples when subjected to the same measurement sequence are quantified by interpolation of their response on the calibration curve.

The operation and timing of device events is controlled by the sequence controller 15b or the CPU 15a. Data acquired from the detectors are processed by the CPU 15a. Results are presented in appropriate concentration units. The results are provided in a readable format, such as on a computer screen or on a hard-copy printout of the results.

Because the sequence of manipulation of the system's components, the volume of reagents and sample, and the timing of the events are all controlled by the CPU 15a and the sequence controller 15b, it is possible to swap from one test to another simply by changing the reagent cartridge (described in greater detail below) and the flow program of the sequence controller 15b. In some cases, it may be necessary to select a different detector 16 or detector conditions for different tests. This too can be automated under control of the CPU 15a. Carryover or cross-contamination from one sample to the next or from one reagent suite to the next is eliminated by including suitable flushing procedures, also under automated CPU control.

Figure 3:
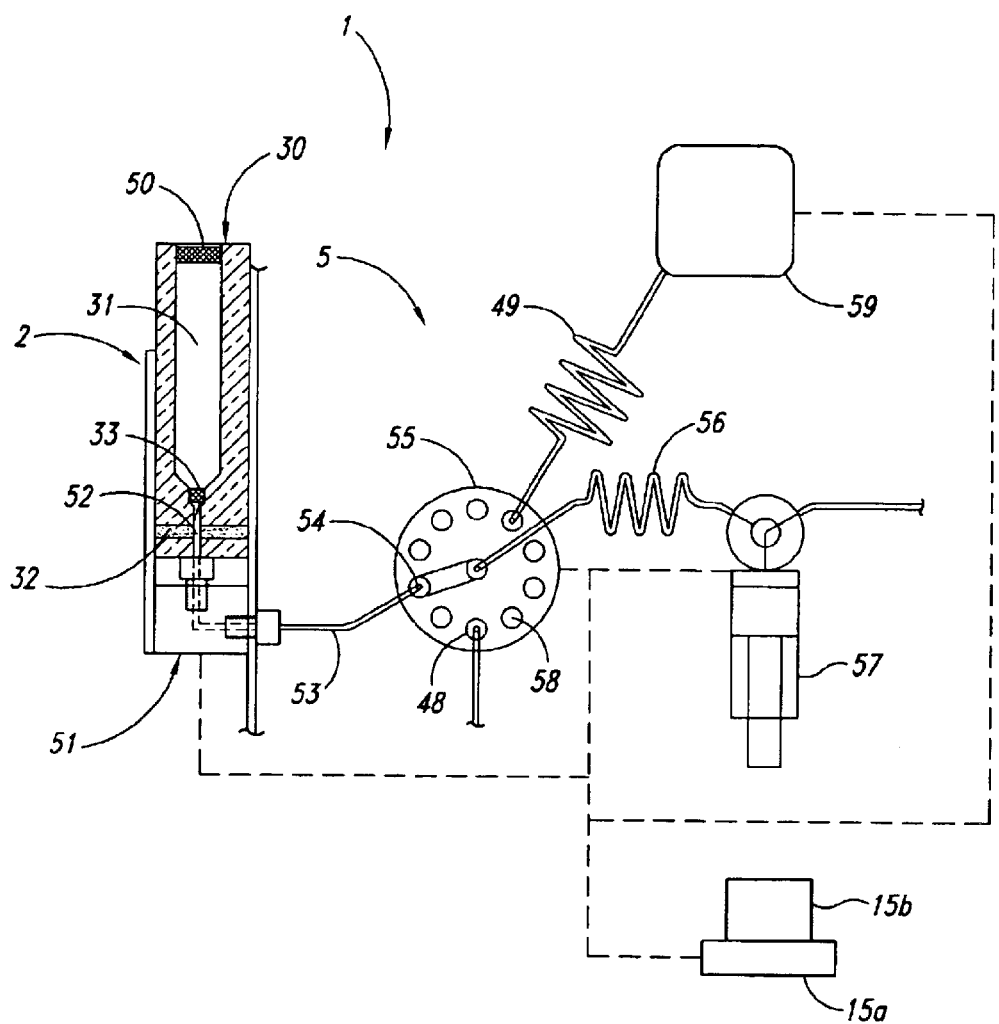
FIG. 3 is a schematic view of an SIA manifold system of an embodiment having a reagent cartridge assembly shown connected to the multi-position valve and the rest of the SIA system.

In the embodiment illustrated in FIG. 3, the SIA testing system 1 has the reagent cartridge assembly 2 with a disposable reagent cartridge 30 (illustrated in FIGS. 6 and 7) that allows reagents to be reconstituted automatically under CPU control using the accurate metering capabilities of the syringe pump 57. The reagent cartridge assembly 2 is removably attached to the SIA assembly 5, so different reagent cartridge assemblies can be used with the same SIA assembly for performing several different medical diagnostic tests. Several reagent reservoirs 31 can be packaged in a disposable reagent cartridge 30. The reagent cartridge 30 is configured to fit onto a mounting bracket 51, shown in FIGS. 4 and 5, having a plurality of hollow needles 52 positioned to extend into the reagent cartridge. Each needle 52 is positioned to align with a respective reagent reservoir 31 when the reagent cartridge 30 is inserted into the mounting racket. The needles 52 are sized to penetrate the septa 32 in the reagent cartridge 30, but not the frits 33 at the bottom of the reagent reservoirs.

The needles 52 are coupled to the multi-position valve 55 (FIG. 3) by short lengths of narrow bore tubing 53 or other suitable flow conduits that form the reagent stream line. Only one cartridge connection is shown for purposes of clarity. Once the reagent cartridge 30 is installed on the mounting bracket 51 and the needles 52 are in fluid communication with the respective reagent reservoirs 31, a reagent makeup sequence, wherein selected reagents are withdrawn from the reagent cartridge 30 in selected volumes, can be initialized for a desired medical diagnostic test using the SIA assembly 5.

As best seen in FIGS. 4 and 5, the mounting bracket 51 has a pair of alignment pins 40 that extend into alignment apertures 41 (FIGS. 6 and 7) in the reagent cartridge 30. The alignment pins 40 and alignment apertures 41 are positioned to align the reagent reservoirs with respective needles 52. This allows for quick installation of the reagent cartridge 30 without misalignment, thereby protecting the needles from being damaged.

In one embodiment, the reagent cartridge 30 is provided with a pre-measured amount of lyophilized reagent or reagent concentrate in a suitable reagent reservoir 31 having a vent 50. The reagent cartridge 30 is dismountably connected to the mounting bracket 51. As indicated above, where needles 52 are used, the needle penetrates the septum 32 but not the porous frit 33.

In one embodiment, the multi-position valve 55 is coupled to a dilutent source that is drawn through the multi-position valve by activation of the syringe pump 57. The syringe pump 57 is used to dispense a metered volume of diluent to the reagent cartridge 30 via the multi-position valve 55. The dilutent fluid passes through the frit 33 and solubilizes the reagent in the chamber 31. If necessary, flow reversal or the bubbling of air through the reagent solution is used to mix the reagent. The porous frit 33 helps to disperse the bubbles introduced to facilitate mixing. It also ensures that no solid particles are aspirated into the flow manifold. Flow reversal is also achieved by the syringe pump 57.

Where bubbles are used to mix the reagent, air is drawn in to the holding coil 56 from one of the ports 58 in the multi-position valve. Then the valve is advanced to the port 54 attached to the reagent cartridge and the bubble is dispensed to the reagent cartridge 30 mixing the solution as it passes through the reagent reservoir 31. A prime sequence is used to flush out any previous solutions in the transfer conduits 53 and primes the multi-position valve 55 with fresh reagent. The device manipulation steps described above are performed under CPU control. The same CPU that controls the rest of the analyzer is used for this. These device manipulation steps are combined to form tasks that are executed by the CPU.

All device events can be grouped together to form tasks. For example, a series of pump and selection valve events could perform the task of metering sample and reagents and moving the resultant zones to an incubator coil, or a length of conduit could be flushed with a buffer solution. Other similar tasks of varying complexity are easily envisaged.

Where one or more tests are simultaneously being carried out on a single apparatus, the sequencing of these tasks becomes a complex undertaking for the CPU to manage. This job is further complicated by variations in the duration of each task, and by some tasks that vary in duration dependent on the composition of the sample. An example of this would be the time that it takes blood to form a clot in a diagnostic test designed to measure clotting time.

Figure 8:
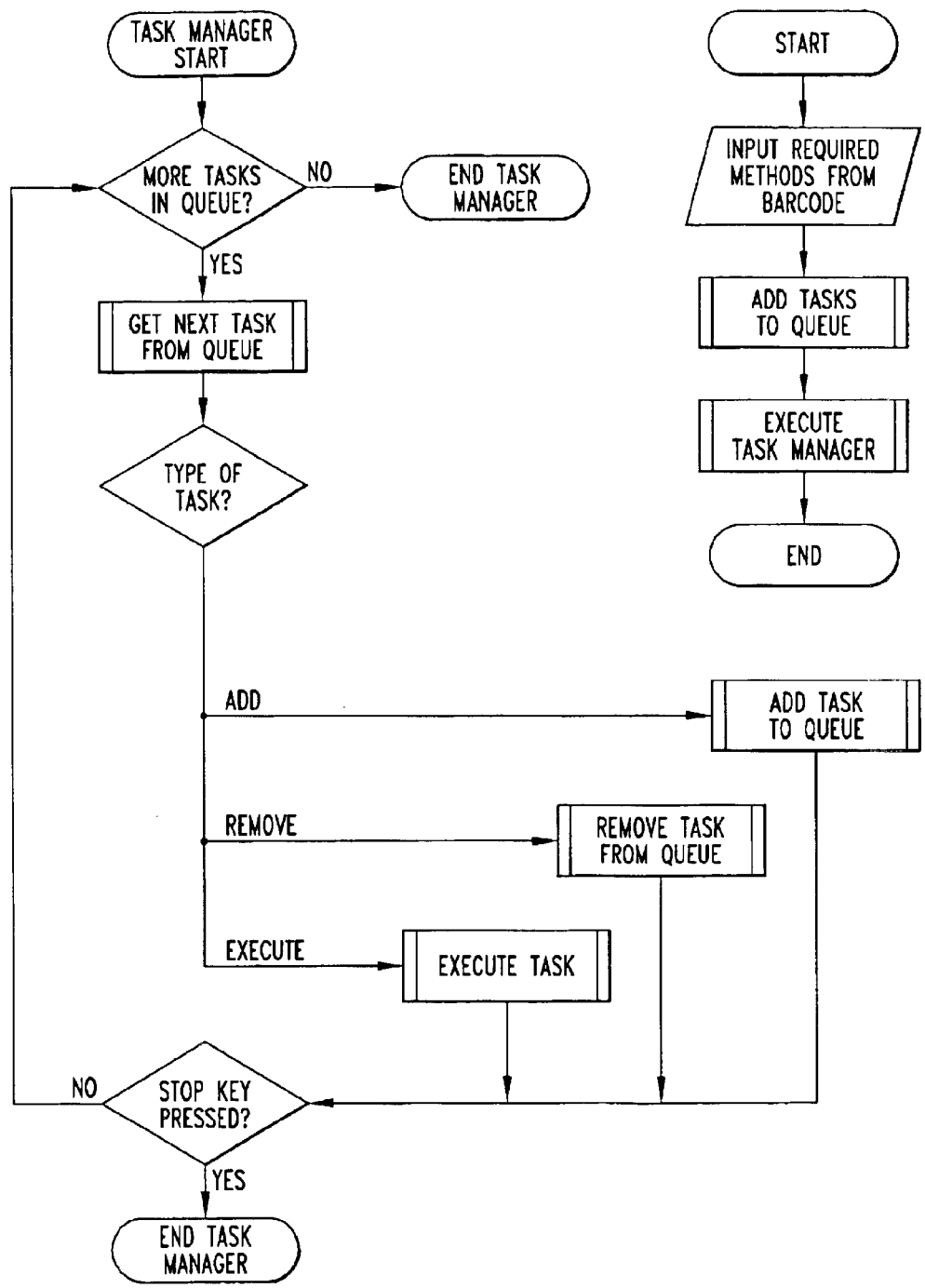
FIG. 8 is a schematic flow chart showing the software algorithm executed by a CPU and sequence controller in the system of FIGS. 1 and 4 for automatically controlling the system's components for performing medical diagnostic tests.

Variation in task duration is not the only complexity to be handled by a sequencing algorithm in accordance with the present invention. In addition, the algorithm is adapted to handle periodic addition or deletion of a test to the suite of tests to be carried out by the apparatus in a particular run. In addition, one test may be carried out more frequently than the next, for example, three tests A, B, and C may be required in the order ABACABAC . . . . The sequencing algorithm described in this invention and given in FIG. 8 accommodates all of these requirements.

The algorithm is based on the implementation of a task manager or sequence controller. The task manager is implemented in the control software as a simple queue. That is to say, new tasks or operation instructions are added to the back of the queue and while there are uncompleted tasks to execute, the next task to be executed is retrieved from the front of the queue and the task is initiated. These tasks include measurement of sample preparations of reagents, priming of multi-position valve (e.g., with the fresh reagent), controlling instrument warm up procedure, instrument calibration, instrument flush-out, and transition between measurement suites. Tasks are first added to the queue after the required tests have been read off an identifier, such as a bar code or other symbology on the reagent cartridge 30. As each task is completed, the task manager retrieves the next task from the front of the queue. Functions are defined in the software that add and remove tasks from the queue. Tasks are added to the queue as they are selected by the user or initialized when a reagent pack is loaded. Tasks are always added to the end of the queue whereas tasks can be removed from any point in the queue.

An important requirement of this algorithm is that each task should end by re-loading the queue with an appropriate task to ensure continued operation of the analyzer. This task will be specified in the test method for each task that goes to make up the test method. In this way, continued measurement is ensured. In most cases, the task simply adds itself to the end of the queue. In due course, the added task will make it to the front of the queue to be executed again. This is repeated until there are no tasks in the queue or the task manager is stopped.

In the case of tasks with an undetermined duration e.g., the time it takes for a clot to form, a function is provided that determines when the task has ended. When the end is detected, this function adds a specified task to the queue that continues or completes the test.

Where anything other than a strict linear sequence of task is required, e.g. to obtain the ABACABAC . . . type sequence, preferred tasks, (A in our example) are simply loaded onto the task manager in the desired sequence, namely ABAC. When the first task A is completed, it ends by adding itself to the back of the queue and task B is executed. It too adds itself to the back of the queue when it is finished, and the second task A is executed. On its completion, it adds itself to the back of the queue and so on with task C.

This invention will apply to a wide variety of medical diagnostic tests. Several examples have been selected to illustrate the breadth of application:

EXAMPLE 1

The determination of heparin by sequential injection titration can be carried out in an automated fashion using this device. Heparin is a naturally occurring substance isolated from porcine intestinal mucosa or bovine lung. Heparin potentiates the inhibitory action of antithrombin III on various coagulation factors including factors IIa, IXa, Xa, XIa, and XIIa. This occurs due to the formation of a complex with and causing a conformational change in the antithrombin III molecule. Inhibition of factor Xa results in interference with thrombin generation; thus, the action of thrombin in coagulation is inhibited. Heparin also increases the rate of formation of antithrombin III-thrombin complex causing inactivation of thrombin and preventing the conversion of fibrinogen to fibrin. By inhibiting the activation of fibrin-stabilizing factor by thrombin, heparin also prevents formation of a stable fibrin clot. Therapeutic doses of heparin prolong thrombin time, whole blood clotting time, activated clotting time, and PTT.

Figure 9:
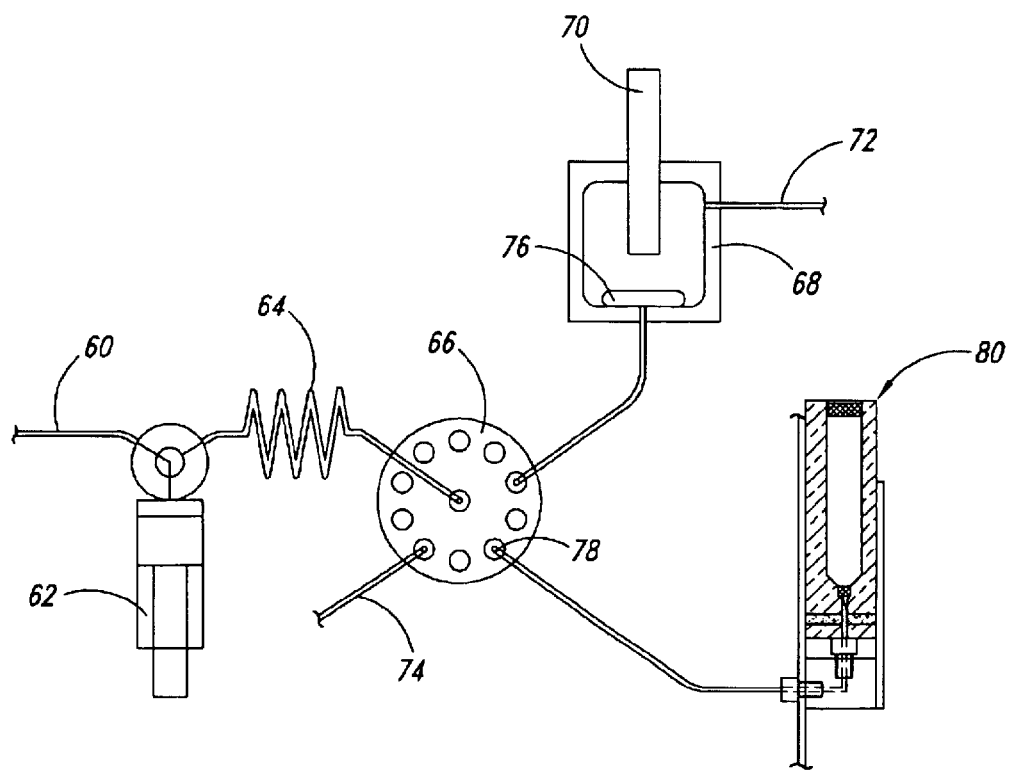
FIG. 9 shows an SIA manifold for performing sequential injection titration.

The manifold used to automate this measurement is equipped as indicated in FIG. 9. In this example, a heparin sensitive electrode 70 is used as the detector. It is placed in a flow cell 68 that is designed to have a high degree of dispersion, such as a stirred chamber. An appropriate reaction coil can be substituted for the chamber. The reagent cartridge assembly is loaded with a disposable reagent cartridge 80 that contains protamine of an appropriate concentration. The protamine is reconstituted by pumping an appropriate volume of buffer into the reagent cartridge 80 using the pump 62 and mixing it by pumping the solution backwards and forwards a few times. Then the multi-position valve 66 is primed with the protamine reagent, the waste being disposed of to a waste container (not shown). About 2 ml of a suitable carrier solution, such as a simple pH buffer is drawn into the pump 62 from a buffer reservoir connected to the pump inlet 60. The multi-position valve 66 is advanced to the reagent port that is primed with protamine. A certain volume of protamine, the titrant, is drawn up into the holding coil 64. The multi-position valve 66 is advanced to the port connected to the sample stream 74, and a smaller volume of sample is drawn into the holding coil 64. The multi-position valve 66 is returned to the port primed with protamine 78 and a similar aliquot to the first zone aspirated is drawn into the holding coil 64 in such a way that the sample is sandwiched between two protamine zones. The multi-position valve is advanced to the detector port and the direction of flow is reversed. The stack of zones is dispensed to the detector flow cell 68.

As the sample zone flows downstream through the flow cell 68, the sample disperses into the titrant zones producing a continuum of heparin/protamine ratios. Therefore, within these two boundaries, an element of fluid can be found where the ratio of the two components is the same. These two equivalence points form a pair. At constant flow, the distance between these two elements is the peak width and it has been shown that the peak width is proportional to concentration of the analyte as long as the width is measured at a fixed height, that is at a constant titrant/titre ratio.

The concentration of the protamine prepared in the reagent cartridge is critical to the success of this measurement. It should be at a level where some but not all of the heparin is the sample is neutralized. By constructing a calibration curve using known concentrations of heparin, the heparin content in unknown samples can be calculated by interpolation.

EXAMPLE 2

The automated SIA test system 1 can be used to determine a wide range of medically significant compounds. In fact a large number of manual ELISA methods have been developed to determine enzymes such as Thrombin, Fxa, Fxia, APC, Plasmin, Single chain t-PA, Plasma Kallikrein, C3a, C5a, TCC Urine Kallikrein Granulocyte Elastase, Trypsin, Streptokinase, Urokinase to name a few. These manual methods are all similar in that they rely on the mixture of certain reagents with the sample to produce a product that can be determined photometrically. Any of these, and many not mentioned, can be determined by this device by simply selecting the appropriate reagent cartridge, loading the cartridge into the SIA test system 1 and performing a selected test. The bar code of the reagent cartridge notifies the CPU which method to load into the sequence controller to perform the desired test.

One compound of interest that can be determined in this way is Protein C. Protein C belongs to the vitamin K-dependent protein group and is synthesized in the liver. Protein C is present in plasma as a pro-enzyme; its transformation into an active enzyme requires the presence of thrombin, calcium and phospholipid. Low levels of protein C are observed at birth due to liver immaturity. The clinical interest of Protein C is the ability to measure the acquired deficiency. The deficiency occurs in patients with hepatic disorders, cirrhosis, and patients with disseminated intravascular coagulation (DIC).

For Protein C, the sequence controller carries out the following steps. After the reagent cartridge is inserted, the reagent preparation tasks are initiated and executed to re-constitute the PC activator that comes from contortix venom and the CBS 65.25 chromogenic substrate. This task ends with the multi-position valve being primed with reagent. Each measurement proceeds as follows. The syringe 57 is filled with a volume of carrier that will be used to flush the reaction products through the flow manifold, and to waste. An isotonic saline buffer is employed as the carrier. The multi-position valve 55 is then advanced to the port 54 that is primed with the PC activator. A small volume of reagent is drawn up into the holding coil 56. The multi-position valve 55 is advanced to the sample port 48 and a small volume of sample is drawn into the holding coil. An incubation time follows after which the multi-position valve 55 is advanced to the CBS 65.25 reagent port (not shown). An appropriate volume of the chromogenic reagent is drawn into the holding coil 56, and the resultant zones are pumped into the reaction coil 49 where the flow is again stopped for a second incubation time. When the incubation time has elapsed, the pump propels the reactants through the flow cell and the detector monitors a change in absorbence at 405 nm as the released p-NA passes through the detector flow cell. The resultant peak shaped response is used to quantify the Protein C by comparing the peak height obtained to the peak heights obtained for calibration samples of know concentration. These calculations are automatically carried out by the CPU (not shown in FIG. 4).

EXAMPLE 3

The preceding two examples have described situations where a single measurement is carried out in the analyzer. Multiple measurements can be carried out in the apparatus by using the sequence controller or task manager. This works as follows. When a multiple chemistry reagent cartridge is inserted into the SIA test system 1, the reagent cartridge's bar code is read and notifies the CPU which tasks to load into the task manager queue. As an example, consider a simple case where two methods are executed, each containing an incubation time after mixture of the reagents as in Example 2. We can then identify four tasks associated with a single measurement of each method; meter zones for method A; meter zones for method B; measure reactants for method A; and measure reactants for method B. During the metering task, reagent and sample zones are drawn into the holding coil and then they are propelled into the reaction coil as described above. Flow is stopped, the metering task just completed is added to the queue and the incubation timer is initiated. The next task is fetched from the queue. This task meters the reagent and sample for method B and positions the reactants in the reaction coil for method B. This reaction coil and detector is coupled to one of the other free ports on the multi-position valve 55 and it has its own flow cell and detector (not shown). When the incubation timer for method A runs out, and if the incubation period for method B has begun, then the pump is free for use by the task that measures the reactants for method A. In the measurement task, the reactants are carried through the flow cell 59, the peak is recorded, and the concentration is calculated. The last step of the measurement task adds the task to the end of the queue. Because each tasks adds itself to the end of the queue at an appropriate point in the task, the sequence of metering and measuring is perpetuated until the operator stops it or the system is shut down.

Although specific embodiments of, and examples for, the present invention are described for illustrative purposes, various equivalent modifications can be made without departing from the spirit or scope of the present invention, as will be appreciated by those of skill in the relevant art. Therefore, the terms used in the following claims should not be construed to limit the invention to the specific embodiments disclosed, but in general should be construed to include all similar testing systems and methods that operate in accordance with the claims. Accordingly, the invention is not limited by this disclosure, but instead its scope is to be determined entirely by the following claims.

What is claimed is:

1. An automated analytical system for sequential-injection sample analysis, the automated analytical system comprising:
   (a) a multipositional stream-selection device;
   (b) a fluid-propulsion device, in fluid communication with the multipositional stream-selection device, for conveying a fluid to and from the multipositional stream-selection device;
   (c) a source of sample, in fluid communication with the multipositional stream-selection device;
   (d) a reagent reservoir containing a lyophilized reagent which is to be dissolved or a solution of reagent which is to be diluted, the reagent, when dissolved in or diluted by a solvent, forms a reconstituted reagent that is capable of reacting with a component of the sample to form a reaction product detectable by the automated analytical system;
   (e) a source of solvent, in fluid communication with the multipositional stream-selection device, for dissolving or diluting the reagent;
   (f) a detector, in fluid communication with the multipositional stream-selection device, for generating a signal indicative of concentration of the component of the sample; and
   (g) a central processing unit, operatively connected to the multipositional stream-selection device, and constructed and arranged for automatic control of fluid flow between the multipositional stream-selection device, the sample source, the reservoir containing the reagent, the solvent source, and the detector.

2. An automated analytical system for sequential-injection sample analysis, the automated analytical system comprising:
   (a) a multipositional stream-selection device;
   (b) a fluid-propulsion device, in fluid communication with the multipositional stream-selection device, for conveying a fluid to and from the multipositional stream-selection device;
   (c) a source of sample, in fluid communication with the multipositional stream-selection device;
   (d) a reagent reservoir containing a lyophilized or a concentrated reagent which, when dissolved in or diluted by a solvent, forms a reconstituted reagent that is capable of reacting with a component of the sample to form a reaction product detectable by the automated analytical system;
   (e) a source of solvent, in fluid communication with the multipositional stream-selection device, for dissolving or diluting the lyophilized or concentrated reagent;
   (f) a detector, in fluid communication with the multipositional stream-selection device, for generating a signal indicative of concentration of the component of the sample; and
   (g) a central processing unit, operatively connected to the multipositional stream-selection device, and constructed and arranged for automatic control of fluid flow between the multipositional stream-selection device, the sample source, the reservoir containing the lyophilized or concentrated reagent, the solvent source, and the detector;
wherein the reagent reservoir includes a porous frit, to facilitate mixing of the solvent with the lyophilized or concentrated reagent, and to prevent residual solids from being drawn from the reagent reservoir with the reconstituted reagent.

* * * * *